(12) United States Patent
Knoepfle et al.

(10) Patent No.: US 10,463,411 B2
(45) Date of Patent: Nov. 5, 2019

(54) SURGICAL RETAINING INSTRUMENTS FOR BONE PLATES

(75) Inventors: Christian Knoepfle, Donaueschingen (DE); Karl Greiner, Muehlheim (DE); Manfred Schmuck, Muehlheim (DE); Uwe Koerner, Muehlheim (DE); Markus Kuhn, Freiburg (DE)

(73) Assignee: Stryker European Holdings I, LLC, Kalamazoo, MI (US)

( * ) Notice: Subject to any disclaimer, the term of this patent is extended or adjusted under 35 U.S.C. 154(b) by 1387 days.

(21) Appl. No.: 13/978,972

(22) PCT Filed: Jan. 12, 2012

(86) PCT No.: PCT/EP2012/000130
§ 371 (c)(1),
(2), (4) Date: Feb. 11, 2014

(87) PCT Pub. No.: WO2012/095318
PCT Pub. Date: Jul. 19, 2012

(65) Prior Publication Data
US 2014/0249585 A1     Sep. 4, 2014

(30) Foreign Application Priority Data

Jan. 14, 2011   (DE) ........................ 10 2011 008 557

(51) Int. Cl.
*A61B 17/17*     (2006.01)
*A61B 17/28*     (2006.01)
*B25B 7/02*      (2006.01)
(Continued)

(52) U.S. Cl.
CPC ........ *A61B 17/808* (2013.01); *A61B 17/1728* (2013.01); *A61B 17/2812* (2013.01);
(Continued)

(58) Field of Classification Search
CPC . A61B 17/808; A61B 17/2812; A61B 17/282; A61B 17/1728; A61B 17/8071;
(Continued)

(56) References Cited

U.S. PATENT DOCUMENTS 3,999,555 A * 12/1976 Person ................. A61N 1/0587
                                                     606/129
4,009,712 A   3/1977 Burstein et al.
(Continued)

FOREIGN PATENT DOCUMENTS

| DE | 197 09 182 A1 | 11/1997 | |
|----|---------------|---------|---|
| DE | 102005029165 A1 | 1/2007 | |
| EP | 1442714 A1 | 8/2004 | |
| FR | 2738475 A1 * | 3/1997 | ......... A61B 17/1728 |
| WO | 9511632 A1 | 5/1995 | |

OTHER PUBLICATIONS

International Search Report for Application No. PCT/EP2012/000130 dated Apr. 19, 2012.

*Primary Examiner* — David W Bates
*Assistant Examiner* — Marcela I Shirsat
(74) *Attorney, Agent, or Firm* — Lerner, David, Littenberg, Krumholz & Mentlik, LLP

(57) ABSTRACT

The invention relates to a surgical retaining instrument for bone plates. The retaining instrument comprises a carrying element and two plate retaining jaws arranged on the carrying element. The mutual distance of the plate retaining jaws can be changed in order to pick up or release a bone plate. Furthermore, an actuating device is provided, which has two arms, which can be moved relative to each other and which are designed to change the mutual distance of the plate retaining jaws. The carrying element is rotatably mounted relative to the arms.

19 Claims, 4 Drawing Sheets

(51) Int. Cl.
  *B25B 7/04* (2006.01)
  *A61B 17/80* (2006.01)
  *A61B 17/00* (2006.01)

(52) U.S. Cl.
  CPC ......... *A61B 17/282* (2013.01); *A61B 17/8071* (2013.01); *A61B 2017/00738* (2013.01); *B25B 7/02* (2013.01); *B25B 7/04* (2013.01)

(58) Field of Classification Search
  CPC ...... A61B 2017/2825; A61B 2017/564; A61B 2017/00738; B25B 7/14; B25B 7/02; B25B 7/04
  USPC .... 606/286; 81/418, 421, 424, 424.5, 426.5, 81/329, 330, 338, 318, 324, 325
  See application file for complete search history.

(56) References Cited

U.S. PATENT DOCUMENTS

| | | | | |
|---|---|---|---|---|
| 5,380,338 | A | * | 1/1995 | Christian ............... A61B 90/50 600/102 |
| 5,423,826 | A | * | 6/1995 | Coates ............... A61B 17/1728 606/281 |
| 8,579,950 | B1 | * | 11/2013 | Jordan ............... A61B 17/8866 606/324 |
| 2002/0147453 | A1 | | 10/2002 | Gambale |
| 2005/0192577 | A1 | * | 9/2005 | Mosca ............... A61B 17/1615 606/86 B |
| 2006/0184197 | A1 | * | 8/2006 | Shifrin .................. A61B 17/12 606/205 |
| 2010/0004691 | A1 | | 1/2010 | Amato et al. |
| 2010/0152789 | A1 | | 6/2010 | Dell'oca |

\* cited by examiner

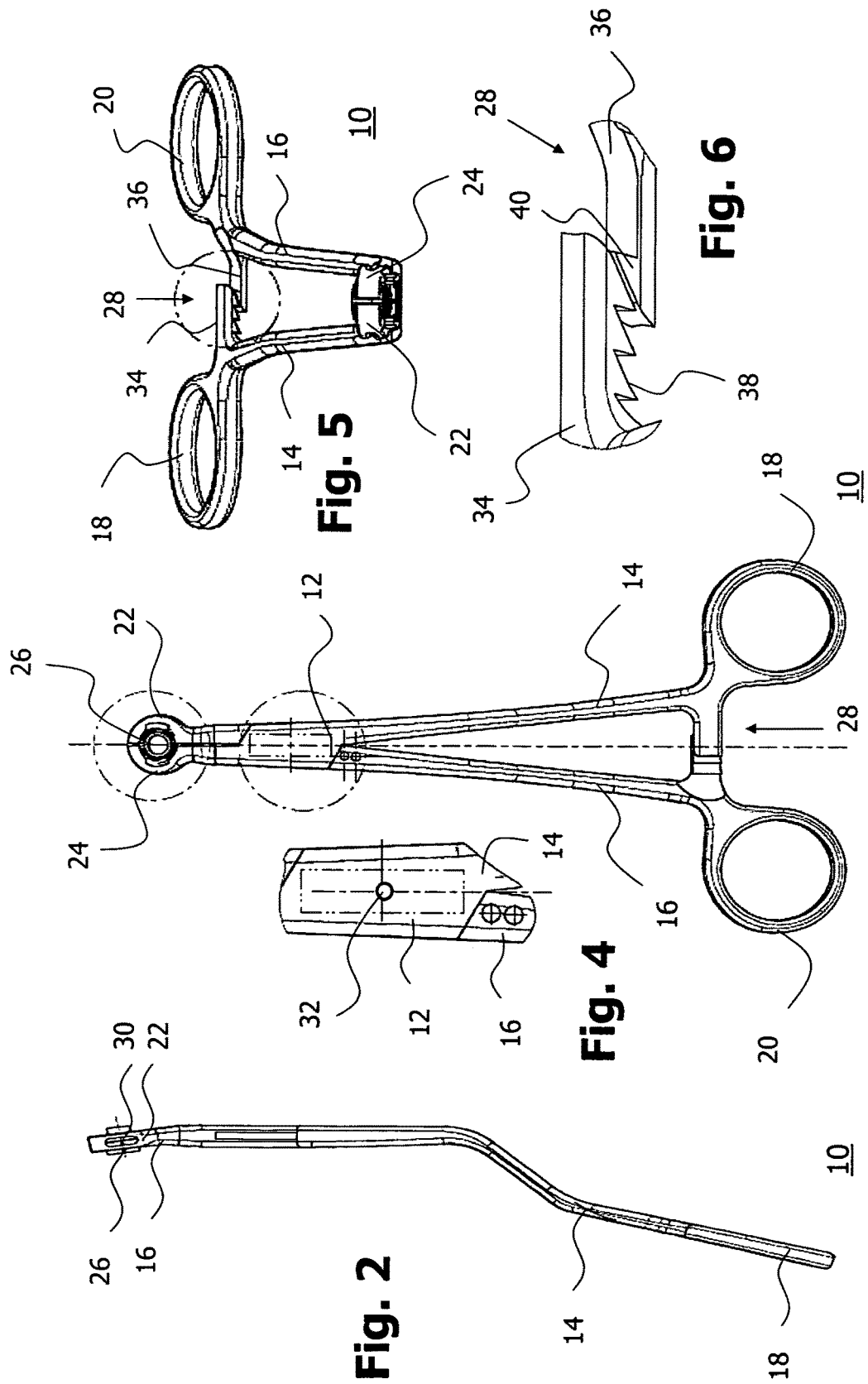

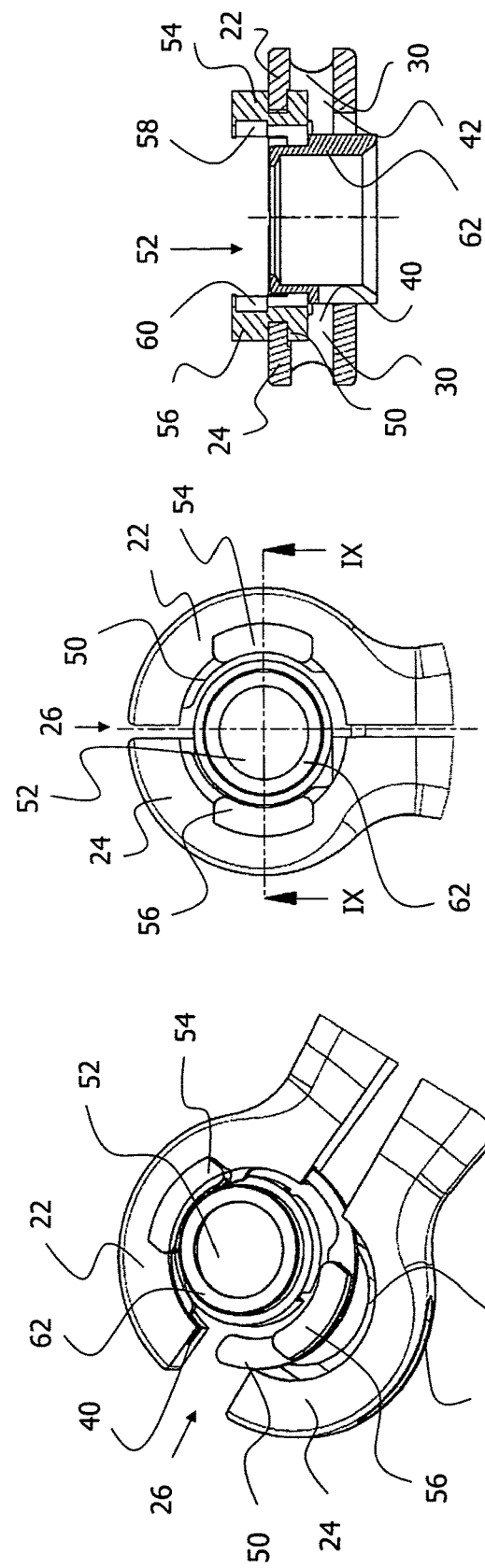

SURGICAL RETAINING INSTRUMENTS FOR BONE PLATES

CROSS-REFERENCE TO RELATED APPLICATIONS

The present application is a national phase entry under 35 U.S.C. § 371 of International Application No. PCT/EP2012/000130 filed Jan. 12, 2012, published in German, which claims priority from German Patent Application No. 10 2011 008 557.2 filed Jan. 14, 2011, all of which are incorporated herein by reference.

BACKGROUND OF THE INVENTION

The present disclosure generally relates to the field of surgical instruments. More specifically, it describes an instrument for retaining bone plates. A retaining instrument for bone plates is known from the document DE 197 09 182 A1 (U.S. Pat. No. 5,755,721). This retaining instrument allows a surgeon to grasp a bone plate that is to be attached to a bone, and place it at the intended attachment position.

The retaining instrument comprises two sleeves, disposed concentrically to one another, that can be moved in opposition. The inner sleeve has two diametrically opposing tongues that extend radially outward at an angle. The inner diameter of the outer sleeve is only slightly larger than the outer diameter of the inner sleeve in the region outside of the splayed tongues. The free end of each tongue is formed as a plate retaining jaw.

Sliding the outer sleeve along the inner sleeve in the direction of the plate retaining jaws causes a relative movement of the two tongues towards one another and therefore of the plate retaining jaws as well. A bone plate disposed between the closing plate retaining jaws is thus clamped by the plate retaining jaws and can be transported to the desired attachment position on the bone using the retaining instrument. In order to release the bone plate after its attachment, the outer sleeve is moved back, away from the retaining jaws, which causes the tongues to spread apart and therefore the plate retaining jaws as well.

The actuating mechanism for the plate retaining jaws described in the document DE 197 09 182 A1 is not without problems in any case. Thus the retaining instrument must be gripped with the first hand, while the second hand actuates the clamping mechanism, that is, displaces the outer sleeve. Handling the retaining instrument known from prior art therefore "occupies" both of the surgeon's hands.

Moreover, it has been found that the sliding movement to release the bone plate occurs very close to the surgical site and therefore cannot always be achieved unhindered. In addition, the surgeon is not always able to reliably grip the outer sleeve and thereby release the bone plate in all surgical scenarios.

BRIEF SUMMARY OF THE INVENTION

There is a need for a surgical retaining instrument for bone plates that comprises an alternative actuating mechanism.

According to one aspect, a surgical retaining instrument for bone plates is suggested comprising a support member, two plate retaining jaws disposed on the support member, the mutual spacing between which can be modified to grasp or release a bone plate, and an actuating device having two relatively movable arms that can be moved towards one another, which are designed to modify the mutual spacing between the plate retaining jaws, wherein the support member is rotatably mounted with respect to the arms.

The support member may be elastically deformable. In this case, the actuating device may be designed to elastically deform the support member in order to modify the mutual spacing between the plate retaining jaws. The resisting force accompanying the elastic deformation can be directed in such a way that the support member (and thereby the plate retaining jaws) is pushed into its initial position. In general, the initial position of the plate retaining jaws can be a release position or a receiving position when the actuating device is not actuated.

The support member can have at least one through-hole. In such an embodiment of the support member, the plate retaining jaws may be disposed on opposing sides of the through-hole on the support member.

For the rotatable mounting of the support member, this support member may have a mounting contour, the encasing end of which is circular. For example, the support member may have a circular mounting contour. The mounting contour may be provided on an outer periphery of the support member.

The support member may be formed as a circular disc or as a ring at least in sections (thus having a through-hole). According to a variant, the support member is formed as a split ring. The split ring can be elastically deformable.

In one implementation of the retaining instrument having a support member that has a through-hole, the retaining instrument may further have a cylindrical sleeve disposed so that it is concentric to the through-hole on the support member. The cylindrical sleeve can perform various tasks. Thus the sleeve can serve as a drill guide or may be designed to accommodate a drill guide. In one embodiment of the drill sleeve as a separate component, it may be removably attached to the cylindrical sleeve (for example with a force-fit, frictionally engaged or form-fit connection).

The rotatability of the support member can be limited to an angular range of less than 360°. For this purpose, the mounting of the support member may be provided with corresponding stops. Alternatively, the support member can also be rotatable over an angular range of more than 360°. In other words, the support member can be designed so that it is freely rotatable.

A mounting provided for the support member can include at least one arch-shaped groove. The groove may be formed in one arm or in both arms of the actuating device. Alternatively or in addition to this, a (possibly complementary) arch-shaped groove may also form the above mentioned mounting contour provided on the support member.

The two arms of the actuating device may be linked to one another in an articulated manner. In general, the arms can be associated with an actuating device formed on the principle of scissors, forceps or tweezers. In the case of a scissors- or forceps-like realization, the joint is formed in a central section of the two arms, while in the case of a tweezer-like realization, the joint connects the two arms at their end section.

The retaining instrument can be ergonomically shaped in various ways. For example, the retaining instrument may comprise angled arms. The arms may be angled approximately in the shape of a Z, for example.

According to one embodiment, the retaining instrument further comprises a locking device in order to lock the mutual position of the arms. Locking the mutual position of the arms may be accompanied by locking or at least impeding the rotatability of the support member. Thus when a bone plate is being grasped, a rotation of the bone plate with respect to the arms of the actuating device can be prevented or at least limited.

According to another aspect, a retaining instrument system is provided, which comprises the retaining instrument described here as well as a bone plate. In the case of the bone plate, it may be a linear plate. The linear plate may have either a curved or a straight form. According to one embodiment, the linear plate may be designed for attachment in the region of the jaw bone.

A contouring of the plate retaining jaws (on the side facing the bone plate) may be selected to correspond to a contouring of the bone plate (on the side facing the retaining jaws). For example, the bone plate may be bulbously contoured (for example in the region of a through-hole for a bone screw). The retaining jaws can, accordingly, each have a bulbously contoured receiving structure for the bone plate.

The system may further comprise a drill sleeve that is used as a guide for a drill and/or for the introduction of a bone screw for attaching the bone plate. In an embodiment in which both the support member and the bone plate each have a through-hole, the retaining instrument can allow the drill sleeve to be accommodated concentrically with regard to both through-holes.

BRIEF DESCRIPTION OF THE DRAWINGS

Further details, advantages and aspects of the retaining instrument and retaining instrument system described herein arise from the following description of an embodiment taken in conjunction with the figures wherein:

FIG. 2 is a side view of the retaining instrument according to FIG. 1;

FIG. 3 is a top view of the retaining instrument according to FIG. 1 in a receiving position;

FIG. 4 is a detail enlargement from FIG. 3 in a joint area;

FIG. 5 is a front view of the retaining instrument according to FIG. 1;

FIG. 6 is a detail enlargement from FIG. 5 in the region of a locking device;

FIG. 7 is a perspective view of the functional end of the retaining instrument according to FIG. 1 in the release position;

FIG. 8 is a top view of the functional end of the retaining instrument according to FIG. 1 in a receiving position;

FIG. 9 is a sectional view of the functional end along the IX-IX line according to FIG. 8;

DETAILED DESCRIPTION

Figure 1:
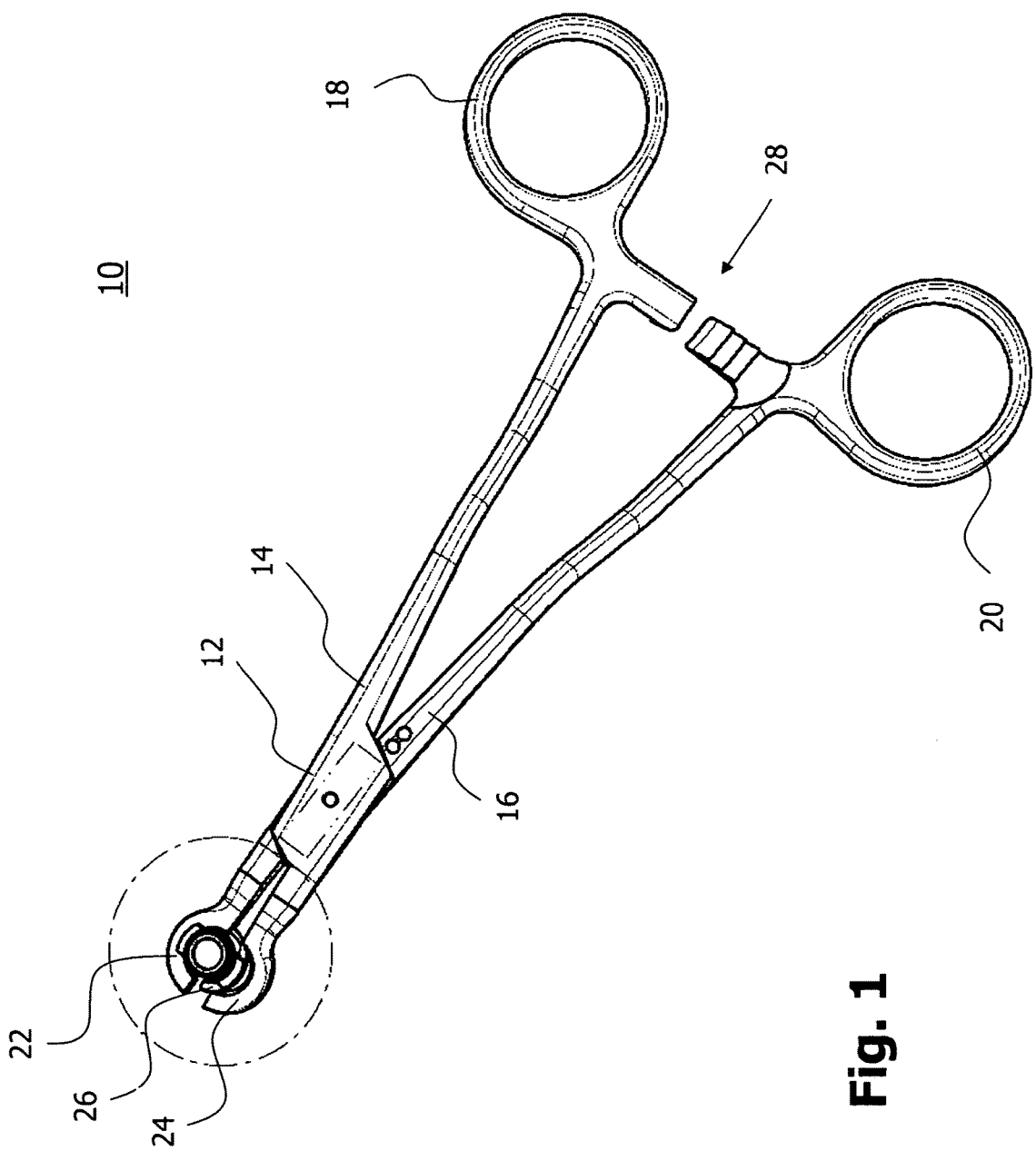
FIG. 1 is a perspective view of an embodiment of a scissors-shaped surgical retaining instrument in a release position.

FIG. 1 shows a perspective view of an embodiment of a scissors-shaped surgical retaining instrument 10. The retaining instrument 10, shown in a receiving position, comprises two arms 14, 16 that are connected to one another in an articulated manner in a central section 12. Each of the two arms 14, 16 has a grip end as well as a functional end.

A finger hole 18, 20 is formed at the grip end of each arm 14, 16 as on a pair of scissors. The arms 14, 16 each have a semi-circularly curved actuation segment 22, 24 on the functional ends opposite the finger holes 18, 22. A locking device 28 is formed in the region of the two finger holes 18, 20. The locking device 28 makes it possible to lock the mutual position of the two arms 14, 16. The operation and structure of the locking device 28 is described in greater detail below with reference to FIGS. 5 and 6.

One of these plate retaining mechanisms 26 that can be actuated is disposed between the two actuation segments 22, 24 in such a way that it is irremovable. The structure and the function of the plate retaining mechanism 26 is described in greater detail below with reference to FIGS. 7 to 9.

FIG. 2 shows a side view of the surgical retaining instrument 10 according to FIG. 2. As illustrated in FIG. 2, the arms 14, 16 of the retaining instrument 10 are angled approximately in the shape of a Z. This angling of the arms 14, 16 makes it easier to handle the retaining instrument 10 in conjunction with the placement of a bone plate that has been grasped, onto a bone.

Clearly recognizable in FIG. 2 is the fact that the actuation segments 22, 24 each have a lateral slot 30 (only the slot 30 of the actuation segment 22 is visible in the side view according to FIG. 2). The slots 30 allow the surgeon to visually check the position of the plate retaining mechanism 26, for example. Moreover, the slots 30 facilitate the entry of a sterilizing medium into the plate retaining mechanism 26.

FIG. 3 shows a view of the plate retaining instrument in a receiving position. For the sake of clarity, the bone plate being grasped is not shown. FIG. 3 clearly shows the fact that the locking device 28 is in the receiving position is in a locked state.

FIG. 4 shows a detail enlargement of the retaining instrument 10 according to FIG. 3 in the region of the central section 12 where the two arms 14, 16 are connected to one another in an articulated manner. As can be seen in FIG. 4, a bearing pin 32 is provided, which defines the pivot point of the two arms 14, 16 relative to each other.

FIG. 5 shows a front view of the retaining instrument in a receiving position, in which the locking device 28 is locked. FIG. 6 shows a detail enlargement from FIG. 5 in the region of the locking device 28. As shown in FIGS. 5 and 6, the locking device 28 comprises two tongue-shaped sections 32, 34.

A first tongue-shaped section 34 is coupled to the arm 14 in the region of the finger hole 18, while a second tongue-shaped section 36 is coupled to the other arm 16 in the region of the other finger hole 20. The two tongue-shaped sections 34, 36 are each provided with serrations 38, 40 on the sides facing one another. The two serrated sections 38, 40 engage in one another when the retaining instrument is moved from the release position shown in FIG. 1 into the receiving position shown in FIG. 3, or in other words when the two arms 14, 16 are moved towards one another. Once the serrated sections 38, 40 have engaged with one another, the relative position of the two arms 14, 16 is locked. In order to release the lock, it is necessary to pivot the two arms 14, 16 in the region of the finger holes 18, 20 relative to one another. This pivoting motion occurs out of the plane of the drawing in the view according to FIG. 3.

The following describes the structure and functioning of the plate retaining mechanism 26 with reference to FIGS. 7 to 9. FIG. 7 shows a detail enlargement of the functional end of the retaining instrument 10 in the release position according to FIG. 1, FIG. 8 shows a detail enlargement of the functional end of the retaining instrument 10 in the receiving position according to FIG. 3 and FIG. 9 shows a side view of the functional end along the IX-IX line in FIG. 8.

As shown in FIGS. 7, 8 and 9, both actuation segments 22, 24 of the two arms 14, 16 are each arch-shaped and inside each comprise a circular-arch shaped groove 40, 42. The two grooves 40, 42 open outward in the region of the slot 30 and thereby clear a view of the plate retaining mechanism 26 incorporated between the two actuation segments 22, 24.

The plate retaining mechanism 26 comprises a support member in the form of a split ring 50 with a through-hole 62. The split ring 50 is elastically deformable. More specifically, the two free portions of the split ring 50 can be compressed towards one another.

Two plate retaining jaws 54, 56 are disposed on the split ring 50 on opposite sides of the through-hole 52. The plate retaining jaws 54, 56 are arched and likewise each have an arched groove on their inner surface for receiving plates 58, 60. In the present embodiment, the contouring of the grooves 58, 60 is selected in accordance with the outer contour of a bone plate that is to be grasped.

The split ring 50, which serves as a support member for the plate retaining jaws 54, 56, is incorporated so that it can rotate freely in the grooves 40, 42 of the actuation segments 22, 24. In so doing, the maximum spacing that the two actuation segments 22, 24 can achieve when the retaining instrument 10 is fully opened is selected in such a way that the split ring 50 (and therefore the plate retaining mechanism 26) is incorporated between the two actuation segments 22, 24 so that it is irremovable.

Figure 11:
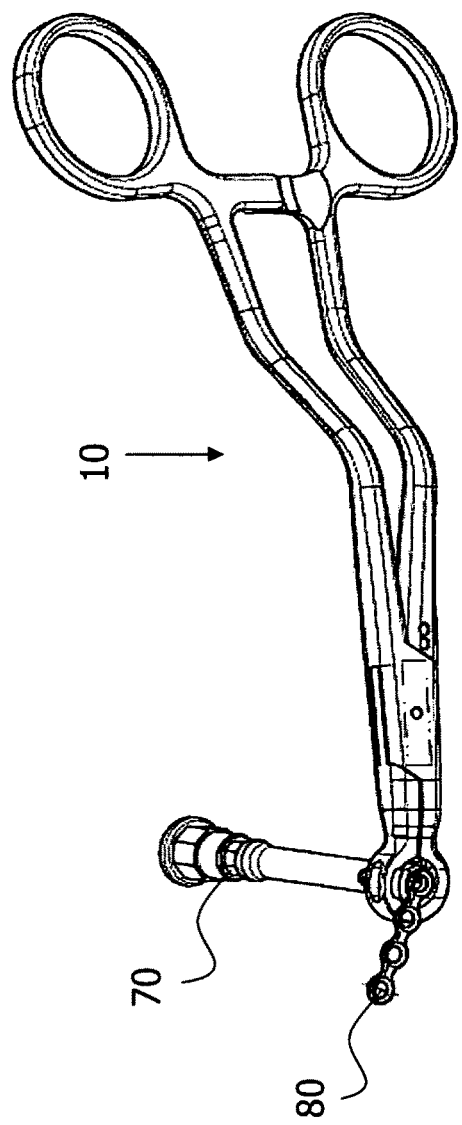
FIG. 11 is a perspective view of an embodiment of a retaining instrument system with retaining instrument, drill sleeve and bone plate.
Figure 10:
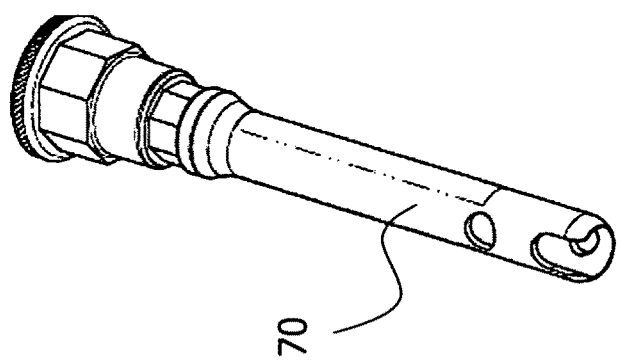
FIG. 10 is a perspective view of a drill sleeve for use with the retaining instrument according to FIG. 1.

The plate retaining mechanism 26 further comprises a cylindrical sleeve 62, which is designed to be concentric to the through-hole 52 of the split ring 50. The cylindrical sleeve 52 is attached in the region on the split ring 50 that is the right retaining jaw 54 in FIG. 7. The cylindrical sleeve 62 serves to accommodate the drill sleeve 70 shown in FIG. 10 with a frictionally engaged connection. FIG. 11 shows the retaining instrument 10 grasping a bone plate 80 and with an inserted drill sleeve 70.

The following will explain the functioning of the retaining instrument 10 in greater detail. Here, it is assumed, by way of example, that the retaining instrument 10 is being used for a transbuccal treatment of a jaw bone. Other uses should not thereby be excluded.

Linear bone plates, like the bone plate 80 schematically shown in FIG. 11, are generally used for the surgical treatment of jaw bones. The bone plate 80 in the embodiment according to FIG. 11 has four through-holes for bone screws, disposed along a straight line. The bone plate 80 has a bulge in the region of each through-hole. Two adjacent bulges are connected to one another by means of a bridge section. As mentioned above, the bulged contouring of the grooves for receiving plates 58, 60 provided in the plate retaining jaws 54, is selected in accordance with the bulged outer contour of the bone plate 80 in the region of a through-hole.

Starting from the release position of the retaining instrument 10 according to FIGS. 1 and 7, the bone plate 80 is positioned in a first step between the two plate retaining jaws 54, 56 in such a way that the plate retaining jaws 54, 56 are disposed in the region of a bulge in the bone plate 80 so that it can be grasped. The through-hole formed in the bone plate 80 for the bone screw is, in this case, disposed so that it is approximately concentric to the through-hole 52 of the split ring 50 as well as to the through-hole of the cylindrical sleeve 62.

The mutual spacing between the two plate retaining jaws 54, 56 in the release position is selected in such a way that the bone plate 80 can be clamped between the two plate retaining jaws 54, 56. In the clamped state, the bone plate 80 is subject to some play, but is disposed between the two plate retaining jaws 54, 56 so that it is irremovable. In this state, the surgeon can freely rotate the bone plate 80 in relation to the arms 14, 16 and align the plate in relation to the jaw bone being treated (and relative to the retaining instrument 10) according to surgical necessity.

In order to finally grasp the bone plate 80 thus positioned, the two arms 14, 16 of the retaining instrument 10 are subsequently moved towards each other while activating the locking device 28. In this context, the actuation segments 22, 24 also move towards one another while compressing the split ring 50. The resisting force associated with the compression of the split ring 50 acts on the serrated segments 38, 40 of the locking device 28 in such a way that the mutual position of the arms 14, 16 and therefore of the plate retaining jaws 54, 56 is locked, free of play.

FIGS. 3, 8 and 11 illustrate the resulting plate-receiving position of the retaining instrument 10, wherein, in FIGS. 3 and 8, the bone plate 80 is not shown for the sake of clarity.

The compression of the split ring 50 by means of the arms 14, 16 causes a movement of the two retaining plate jaws 54, 56 towards one another and consequently, a clamping of the bone plate 80 disposed between the two plate retaining jaws 54, 56. Moreover, the compression of the split ring 50 increases the force fit or the frictional connection between the split ring 50 as well as the actuation segments 22, 24, which accommodates and holds the split ring 50. For this reason, the split ring 50 and therefore the bone plate 80 being grasped as well, are fixed between the two actuation segments 22, 24 so that they are essentially rotationally fixed.

In the receiving position, the rotatability of the split ring 50 in the receiving grooves 40, 42 of the actuation segments 22, 24 can be maintained to a limited extent. The surgeons can then (with increased force) still turn the grasped bone plate 80 with respect to the retaining instrument 10 to a certain extent, and finally align it according to surgical needs with respect to the jaw bone being treated.

The drill sleeve 70 is placed over the cylindrical sleeve 62 either prior to or subsequent to grasping and aligning the bone plate 80. In the receiving position, which is illustrated in FIG. 11, the through-holes of the drill sleeve 70, of the cylindrical sleeve 62, and as well as of the split ring 50 are disposed concentrically with respect to a through-hole of the bone plate 80.

In the next step, the bone plate 80 is positioned on the jaw bone via a transbuccal route using the retaining instrument 10. A pilot hole is subsequently drilled using the drill, which is guided through the drill sleeve 70. Subsequent to the formation of the pilot hole, a bone screw is introduced into the jaw bone through the drill sleeve 70. The bone plate 80 is attached (at least temporarily) to the jaw bone using this bone screw. After the bone plate 80 has been attached, the locking device 28 is released by pivoting the two arms 14, 16 relative to one another in the region of the two finger holes 18, 20. The two plate retaining jaws 54, 56 move away from one another due to the resisting force exerted by the compressed ring 50, and the bone plate 80 is released. The plate retaining instrument 10 can then be removed from the surgical site via a transbuccal route.

As is apparent from the above description of a preferred embodiment, the handling of the retaining instrument described here is made easier, since the surgeon can both grip the plate using a single hand, and manipulate the actuating mechanism in order to grasp and release the bone plate. Moreover, the actuating mechanism is manipulated at the distal end of the retaining instrument facing away from the surgical field. This fact further facilitates the handling of the retaining instrument. However, other implementations of the plate retaining instrument presented here are conceivable, which do not or do not fully realize these aspects. Moreover, numerous developments of the plate retaining instrument are possible. Thus, for example, a light source could be provided on the retaining instrument (fiber optic, for example), which would illuminate a region around the actuation segments 22, 24.

The invention claimed is:

1. A surgical retaining instrument for bone plates, comprising:
   a plate retaining mechanism having a support member;
   first and second plate retaining jaws disposed on the support member, the mutual spacing between which can be modified to grasp or release a bone plate; and
   an actuating device having first and second arms that can be moved in relation towards one another, which first and second arms respectively include an actuation segment designed to modify the mutual spacing between the plate retaining jaws, wherein the support member is rotatably mounted with respect to the arms; and
   wherein the plate retaining mechanism is disposed between the two actuation segments of the arms, and the rotation of the support member takes place therebetween, the support member being rotatable about a rotation axis perpendicular to a direction in which the first and second arms can be moved in relation towards one another,
   wherein the support member is mounted to the first arm so as to be capable of rotating about the rotation axis over an angular range of more than 360° prior to the first and second jaws grasping the bone plate.

2. The retaining instrument according to claim 1, wherein the support member is elastically deformable and the actuating device is designed to elastically deform the support member in order to modify the mutual spacing between the plate retaining jaws.

3. The retaining instrument according to claim 1, wherein the support member has a through-hole and the plate retaining jaws are disposed on opposing sides of the through-hole on the support member.

4. The retaining instrument according to claim 3, further comprising a cylindrical sleeve disposed concentrically to the through-hole on the support member.

5. The retaining instrument according to claim 4, wherein the sleeve is designed as a drill guide or to accommodate a drill guide.

6. The retaining instrument according to claim 1, wherein the support member has a mounting contour, which is arcuate.

7. The retaining instrument according to claim 1, wherein the support member is formed as a ring, at least in sections.

8. The retaining instrument according to claim 1, wherein each arm actuator segment has a bearing surface provided for receiving the support member, the bearing surface comprising an arch-shaped groove.

9. The retaining instrument according to claim 1, wherein the first and second arms are connected to one another in an articulated manner.

10. The retaining instrument according to claim 1, wherein the first and second arms are connected in a manner allowing corresponding ends of each arm to move towards and away from each other.

11. The retaining instrument according to claim 1, wherein the retaining instrument is angled approximately in a Z-shape.

12. The retaining instrument according to claim 1, further comprising a locking device in order to lock the mutual position of the arms.

13. A retaining instrument for bone plates, comprising:
    a bone plate retaining mechanism having an elastically deformable support member;
    the elastically deformable support member having first and second bone plate retaining jaws, the mutual spacing between which can be modified to grasp or release a bone plate;
    an actuating device having first and second arms that receive the support member and can be moved in relation towards one another, which are designed to modify the mutual spacing between the plate retaining jaws, wherein the support member is rotatably mounted with respect to the first arm prior to grasping a bone plate and the rotation of the support member takes place in between the first and second arms, the support member being rotatable about a rotation axis perpendicular to a direction in which the first and second arms can be moved in relation towards one another; and
    wherein the support member is elastically deformable by movement of the first and second arms towards one another,
    wherein the support member is mounted to the first arm so as to be capable of rotating about the rotation axis over an angular range of more than 360° prior to the first and second bone plate retaining jaws grasping the bone plate.

14. The retaining instrument according to claim 13, wherein the bone plate is a linear plate.

15. The retaining instrument according to claim 13, wherein a contouring of the plate retaining jaws is selected to engage with a contouring of the bone plate.

16. The retaining instrument according to claim 15, wherein the bone plate is bulbously contoured.

17. The retaining instrument according to claim 13, further comprising a drill sleeve, wherein the support member and the bone plate each have a through-hole and the retaining instrument allows the drill sleeve to be accommodated concentrically and in relation to both through-holes.

18. A surgical retaining instrument for grasping a bone plate comprising:
    a split-ring;
    the split-ring having first and second plate retaining jaws thereon at separate locations spaced around a circumference of the split-ring, a distance between the first and second jaws can be modified by deformation of the split-ring to grasp or release a bone plate; and
    an actuating device having first and second arms that can be moved towards one another, the first and second arms are designed to inwardly deform the split-ring to modify the spacing between the plate retaining jaws for grasping the bone plate, wherein the split-ring is rotatably mounted on the first arm so as to be capable of rotating in between the first and second arms over an angular range of more than 360° prior to movement of the first and second arms towards one another to grasp the bone plate, the split-ring being rotatable about a rotation axis perpendicular to a direction in which the first and second arms can be moved towards one another.

19. The surgical retaining instrument as set forth in claim 18, wherein the split-ring is elastically deformable by the movement of the first and second arms toward one another.

* * * * *